United States Patent
Soloviev et al.

(10) Patent No.: US 6,451,850 B1
(45) Date of Patent: Sep. 17, 2002

(54) BIO-CHEMICAL GERMANIUM COMPLEXES WITH HIGH THERAPEUTIC EFFICIENCY AND WIDE APPLICATION SPECTRUM

(75) Inventors: Evgeny Vladimirovich Soloviev, 2, rue des Capucins, F-92190, Meudon (FR); Vladimir Viktorovich Shcherbinin, Leninsky prosp., 83, art. 46, Moscow, 117261 (RU); Evgeny Andreevich Chernyshev, Leninsky prosp., 61/1, art. 54, Moscow, 117333 (RU); Mikhail Vladimirovich Kotrelev, ul. B. Bronnaya, 5, art. 12, Moscow, 103104 (RU); Konstantin Vitalevich Pavlov, Moscow (RU); Nataliya Yurievna Khromova, Moscow (RU); Nina Georgievna Komalenkova, Moscow (RU)

(73) Assignees: Evgeny Vladimirovich Soloviev, Meudon (FR); Vladimir Viktorovich Shcherbinin, Moscou (RU); Evgeny Andreevich Chernyshev, Moscou (RU); Mikhail Vladimirovich Kotrelev, Moscou (RU)

( * ) Notice: Subject to any disclaimer, the term of this patent is extended or adjusted under 35 U.S.C. 154(b) by 0 days.

(21) Appl. No.: 09/763,222
(22) PCT Filed: Aug. 17, 1998
(86) PCT No.: PCT/EP98/05214
§ 371 (c)(1),
(2), (4) Date: May 14, 2001
(87) PCT Pub. No.: WO00/10561
PCT Pub. Date: Mar. 2, 2000
(51) Int. Cl.$^7$ .............................................. A61K 31/28
(52) U.S. Cl. ...................................... 514/492; 514/262
(58) Field of Search .......................... 424/650; 514/262, 514/492

(56) References Cited

U.S. PATENT DOCUMENTS

| 4,772,628 A | | 9/1988 | Kaimoto et al. | |
|---|---|---|---|---|
| 4,919,917 A | * | 4/1990 | Kakimoto et al. | ............ 424/10 |

FOREIGN PATENT DOCUMENTS

| EP | 0186505 A2 | 7/1986 |
|---|---|---|
| EP | 0369776 A2 | 5/1990 |
| JP | 60011494 | 1/1985 |
| JP | 61158989 A | 7/1986 |
| SU | 60011494 | 10/1993 |
| WO | WO 98/40103 | 9/1998 |

OTHER PUBLICATIONS

McMaster et al, New Drugs, vol. 8, pp. 87–92, Feb. 1990.*
Goodman, *Therapeutic Effects of Organic Germanium*; Medical Hypotheses, 26, pp. 207–215, Longman Group, U.K., Ltd., 1998.

* cited by examiner

*Primary Examiner*—James H. Reamer
(74) *Attorney, Agent, or Firm*—Greer, Burns & Crain, Ltd.

(57) ABSTRACT

The present invention applies to medicine, more specifically, to pharmacology and it can be applied for the expansion of therapeutic effects spectrum, strengthening of therapeutic effect and a decrease of medicaments' toxicity. For realization of the method, a patient is treated with a medicament complex with derivatives of 1-germa-2,8,9-trioxa-5-azatricyclo[3.3.3.0$^{1.5}$]undecane or with derivatives of 1-germa-2,8 dioxa-5 azabicyclo[3.3.0$^{1.5}$]octane in doses of 0.001÷0.1 g per day. In doing so, biologically active compounds which are contained in food products, in hygienic and cosmetic remedies, in medicinal herbs and plants can be used as a medicament component. The method allows a considerable increase of complex pharmacological activity of medicaments for a wide diversity of diseases and decrease of the medicaments' toxicity.

24 Claims, 1 Drawing Sheet

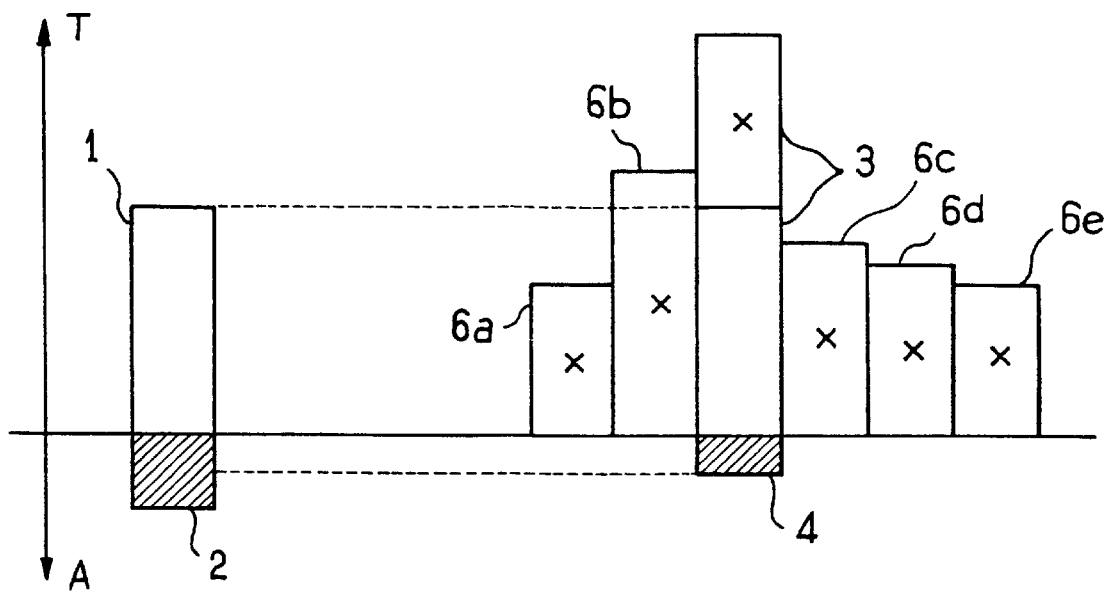
FIG_1
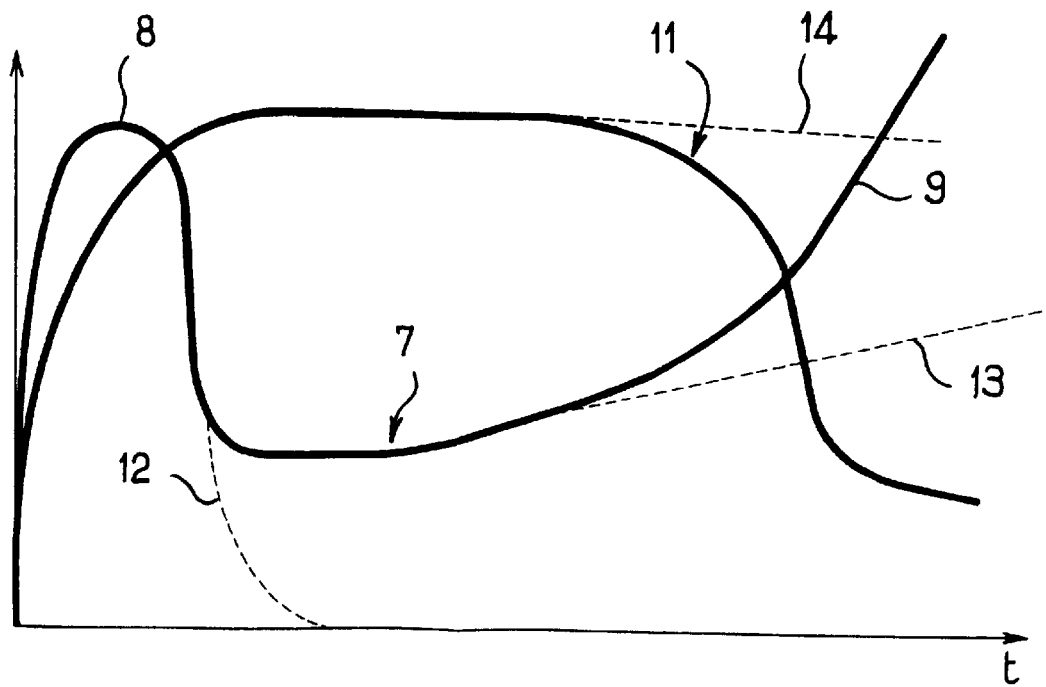
FIG_2

BIO-CHEMICAL GERMANIUM COMPLEXES WITH HIGH THERAPEUTIC EFFICIENCY AND WIDE APPLICATION SPECTRUM

SPHERE OF TECHNOLOGY

The present invention applies to medicine, more specifically, to pharmacology and it can find applications in pharmacotherapy for all kinds of diseases including decrease of organism intoxication under taking medicines.

PREVIOUS LEVEL OF TECHNOLOGY

A search for ways of strengthening of medicines action on the human organism goes on for a long time. It is connected both to insufficient therapeutic effect of the compound and to its insufficient quantity which is applied for treatment and cannot be increased owing to onset of its toxic effect as far as practically all the compounds exert an adverse effect including non-allergic negative side effect, allergic reactions, toxic effects, etc. [1]. Manifestations of non-allergic side effect include only the effects which appear under application of compounds in therapeutic doses and compose a spectrum of their pharmacological action. Thus, under application of tranquilizers quickness of mental and-physical reactions decreases, sleepiness appears; in the case of analgetics, e. g., acetylsalicylic acid, ulcerogenic action and other side effects are observed.

Side effects can be primary and secondary ones. The primary effect appears as a direct result of the present medicine influence on a certain substrate (e. g., nausea, vomiting under an irritating action of a compound on a mucous membrane of the stomach). The secondary side effect concerns unfavorable side influences (e. g. hypovitaminosis as a result of intestinal flora suppression with antibiotics) [1]. Unfavorable effects of compounds are highly diverse by their character; they have unequal expression and different duration. Side effects can be directed towards the nervous system, blood and hematogenesis, blood circulation organs, respiration, digestion, kidneys, endocrine glands, etc. Some side effects are endured relatively easily (moderate nausea, headache, etc.), other ones can be serious and even dangerous for life (liver affection, leucopenia, aplastic anemia) [1]. Negative influences exerted by medicaments also include allergic reactions, frequency of which is high enough. They appear independently from the dose of applied compound [1]. Clinical picture of allergic reactions is very different. There can appear urticaria and other skin erruptions, angioneurotic edema, serum sickness, bronchial asthma, breach of hemopoiesis, fever, hepatitis, cholestatic jaundice, anaphylactic shock, etc. [1].

Idiosyncrasy is another possible cause of unfavorable responses to compounds. Compounds cause toxic effects in doses over therapeutic ones. The last named generally manifest themselves as some serious breaches of functions of organs and systems (hearing decrease, vestibular disturbances, blindness as a result of optic nerve lesion, an expressed breach of stimulation conduction via the myocardium, liver lesion, breach of hemopoiesis, suppression of vitally important centers of medulla oblongata). The main cause of toxic effects is overdosage—occasional or deliberate exceeding of maximum permissible doses. Moreover, accumulation of toxic concentrations of compounds in the organism is possible as a result of breaches of their metabolism (e.g., under liver pathology) or under slow excretion of these (under some kidney diseases). Being prescribed during pregnancy medicaments can exert a detrimental effect on the embryo and fetus. Such effects include teratogenic impact of compounds, which causes birth of children with various anomalies [1]. Medicaments can possess mutagenous and embryotoxic properties. These properties are especially intrinsic for antitumoral agents. In the case of some compounds drug dependence can develop under repeated application. It manifests itself as irresistible yearning for application of the compounds, usually with the aim of improvement of mood or with the purpose to feel better, to get rid of suffering or unpleasant senses and feelings including ones which appear under abolition of compounds causing the drug dependence.

Psychical drug dependence and physical one are recognized. In the case of psychical drug dependence discontinuance of the drugs application (e. g., cocaine or hallucinogens) leads only to emotional discomfort. Under application of some compounds physical drug dependence can be in progress. In this case abolition of the drug causes grave condition which, in addition to acute psychical changes, manifests itself as various and often serious somatic breaches connected to functional disorder of many systems of the organism. This is the so called abstinence syndrome or deprivation phenomenon [1]. A search of ways for reduction of unfavorable effects of medicaments goes on for a long time. A big number of compounds for the specific treatment of drug poisoning, which are called antidotes and antagonists, include compounds which inactivate poisons either via chemical and physical interaction or at the sacrifice of pharmacological antagonism (at the level of physiologic systems, receptors, etc.). Thus, under intoxication with heavy metals, compounds are applied which form non-toxic complexes with the metals (e.g., unithiol, penicillamine, $CaNa_2EDTA$). Antidotes are known, which react with the compound and release the substrate (e. g., oximes, which are cholinesterase reactivators; antidotes, which are applied under intoxication with methemoglobin formers, act in a similar way). Pharmacological antagonists are of considerable use under acute poisonings (atropine—under poisoning with anticholinesterase agents, naloxone—under poisoning with morphine, etc.). Pharmacological antagonists usually enter into competitory interactions with the same receptors, which interact with the compounds which caused the poisoning [1]. However, antidotes and antagonists are specific compounds characteristic for a specyfic type of intoxications and these are not applied under application of medicaments in therapeutic doses [1]. Antidotes and antagonists are not applied as complexes with medicaments.

To expand medicaments effect spectrum and promote pharmacological effect of compounds and decrease their toxicity, compounds with various composition were investigated including organogermanium ones.

Among organogermanium compounds (OGC), therapeutic effect of 2-carboxyethyl-germanium sesquioxide $(O_{1.5}GeCH_2CH_2COOH)_n$ and its derivatives has been much investigated. Authors applied this compound and its derivatives as original medicaments. There exist examples of its applications in cosmetics, as a nutrition additive and as an original medicament [2]. 2-Carboxyethylgermanium sesquioxide and its derivatives have been much investigated as original anticancerogenic medicaments in clinics and found not sufficiently powerful [2].

The medicament manifested therapeutic effect in high doses, usually 100–200 mg/day, what, as it has been found later, leads to various health breaches [2]. The authors have not claimed a universal effect for expansion of the medicaments effect spectrum, strengthening of pharmacological effect of the compounds and decrease of the drug toxicity [2–11].

To promote the main pharmacological effect, medicaments are often applied on the background of various stimulants (e. g., specific antibacterial therapy on the background of immunostimulation).

Applied in therapeutic practice, immunopotentiators are the closest by their effect to the claimed compounds.

Medicaments, which stimulate (normalize) immune reactions, are applied in complex therapy of immunodeficient states, chronic infections and malignant tumors. Biogenic substances are applied as immunopotentiators (thymus preparations, interferon, BCG vaccine) and synthetic compounds (Levamisolum, sodium diethylthiocarbamate, etc.) [1].

Tactivinum (T-activin) normalize quantity and function of T-lymphocytes (in immunodeficient states), stimulates production of lymphokines, α- and β-interferons, rehabilitates suppressed production of T-killers and in general increases cell immunity tension. It is applied in immunodeficient states (after radiotherapy and chemotherapy for oncologic patients, under chronic purulent and inflammatory processes, etc.), under lymphogranulomatosis and also under disseminated sclerosis [1].

Interferon is known mainly thanks to its antiviral activity. At the same time it has been shown that it causes favorable influence on the course of immune processes. In combination with another medicaments it is applied in therapy of some infections (e. g., hepatitis) and also neoplasms (especially under myeloma and lymphoma from B-cells) [1].

The BCG vaccine is applied for vaccination against tuberculosis. At the present time the BCG vaccine is applied in complex therapy for a number of malignant tumors.

The BCG vaccine stimulates macrophages and, obviously, T-lymphocytes. Favorable effect has been recorded under acute myeloid leukemia, some kinds of lymphoma (unrelated to Hodgkin's lymphoma), under cancer of intestine and mammary glands [1].

Levamisolum (Decaris) belongs to synthetic preparations. It is applied in the form of hydrochloride. There are indications that Levamisolum causes stimulating influence on macrophages and T-lymphocytes. It does not modify production of antibodies. Consequently, the main effect of Levamisolum manifests itself in normalization of the cellular immunity. It is applied under immunodeficient states, some chronic infections and a number of tumors.

Levamisolum is prescribed in combination with specifically effecting preparations. It is applied inwardly. After its single taking side effects practically are not observed. At the same time after repeated takings of Levamisolum, especially if its doses are high, many side effects are observed, including more serious ones. Thus, allergic reactions can manifest themselves (eruption, fever, stomatitis), suppression of hemopoiesis (neutropenia, agranulocytosis). Besides, neurological breaches are observed (excitement, insomnia, headache, vertigo) and dyspeptic effects (nausea, vomiting, diarrhea) [1].

However, none of the immunopotentiators being used does exhibit any universal expansion of the medicaments effect spectrum, strengthening of pharmacological effect of the compounds and decrease of the drug toxicity.

All the immunopotentiators listed here possess side effects and are unsuitable for long and constant use. [1]. The method by the source [1] is taken as the prototype for the claimed method.

DISCLOSURE OF THE INVENTION

The present invention allows to overcome the above mentioned shortcomings of Levamisolum application and to ensure expansion of the medicaments effect spectrum, strengthening of pharmacological effect of the compounds and decrease of the drug toxicity for medicaments both of organic origin and of inorganic one independently of the kind of medicament and the kind of disease.

According to the invention, there is provided a substance for human and animal use, e.g., for therapeutic, prophylatic, alimentary or hygienic purposes comprising a complex of at least one medicament or biologically active compound with at least one chemical compound, characterized in that the chemical compound comprises an organogermanium compound (OGC) and the complex has the general formula (I):

$$L_k(OGC)_m(Solv.)_n \quad (I)$$

Where $k \geq 1$ $m \geq 1$ $n \geq 0$

L: a medicament or a biologically active compound

Solv.: an inorganic or organic solvent

It has been found that complexes of medicaments with organogermanium compounds remarkably expand drug action spectrum, promote pharmacological effect and decrease drug toxicity of both the medicament and the organogermanium compound.

Preferably, said organogermanium compound corresponds to 1-germa-2,8,9-trioxa-5-azatricyclo[$3.3.3.0^{1,5}$] undecane having a general formula (II):

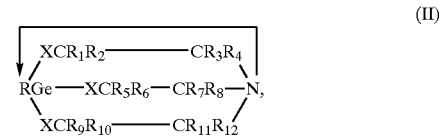

(II)

where:

R—an organic radical or hydroxyl or thiohydroxyl or elementoorganic radical $R_1 \div R_{12}$—hydrogen or an organic radical, oxygen (under substitution of $R_1R_2$; $R_5R_6$; $R_9R_{10}$);

X=oxygen or sulfur.

According to another embodiment of the invention, the organogermanium compound corresponds to:

1-germa-2,8-dioxa-5-azabicyclo[$3.3.0^{1,5}$]-octane having the general formula (III):

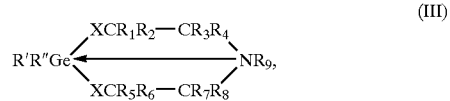

(III)

where

R'R"; an organic or elementoorganic radical, $R_1$–$R_9$: hydrogen or an organic radical, oxygen (by substitution of $R_1R_2$, $R_5R_6$)

The main types of medicaments and biologically active substances do compound with organogermanium groups. Taking the example of 1-germa-2,8,9-trioxa-5-azatricyclo [$3.3.3.0^{1,5}$]undecane, the chemical interaction can be explained according to the following three main types of interactions:

1. Formation of hydrogen bonds between the hydroxyl (thiohydroxyl) group of an OGC and hydroxy-, carboxy-, oxo-, amino-, sulpho-, mercapto- and other groups, and also their thioanalogs, anions of organic and inorganic salts and other groups of medicaments and biologically active compounds.

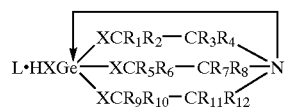

2. Expansion of coordination sphere of the germanium atom up to 6 as a result of donor-acceptor interaction of functional groups of medicaments and biologically active compounds mentioned in Item 1 with the atom of germanium.

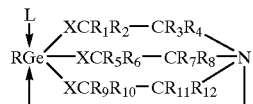

3. Donor-acceptor interaction of the nitrogen atom in the molecule of an OGC with carboxy(thiocarboxy)group of a medicament or a biologically active compound.

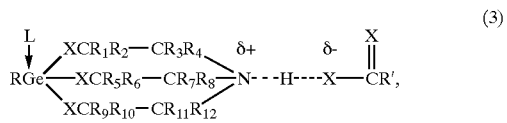

(3)

where R': an organic radical.

Mixed types of such complexes can also be observed. Application of complex compounds of medicaments (L) with OGC having the general formula (I, II or III) leads to substantial expansion of the medicaments effect spectrum, strengthening of pharmacological effect of the compounds and decrease of toxicity of medicaments and biologically active compounds.

Complex medicaments, in addition to their pharmacological effect, acquire the following pharmacological properties: antitoxic, antiinflammatory, antihypoxic, immunopotentiating, repairing, nootropic ones. If the medicament already possesses the listed pharmacological properties, so the listed pharmacological properties will be considerably strengthened. The main pharmacological property of the medicament will also be strengthened.

Hypoxy, stimulation of lipids peroxide oxidation, immunodepression, development of inflammatory processes are universal mechanisms for development of practically any pathology. Thus, a complex medicament blockades various stages of disease development, increases resistance of the organism resulting in strengthening of the main therapeutic effect and also in decrease of the complex medicament toxicity. Expansion of medicament effect spectrum, strengthening of therapeutic effect and decrease of toxicity are observed on formation of complexes with any one of medicaments and biologically active compounds: aminoacids, vitamins, nucleic acids and their components, carbohydrates, lipids, fatty acids, ferments, hormones, steroids, porphyries, etc.

The following compounds are applied as the organogermanium part of the complex: 1-hydroxy-1-germa-2,8,9-trioxa-5-azatricyclo[3.3.3.0$^{1,5}$]undecane, 1-thiohydroxy-1-germa-2,8,9-trioxa-5-azatricyclo[3.3.3.0$^{1,5}$]undecane, 1-methyl-1-germa-2,8,9-trioxa-5-azatricyclo[3.3.3.0$^{1,5}$] undecane-3,7-dione, 1-methyl-1-germa-2,8,9-trioxa-5-azatricyclo[3.3.3.0$^{1,5}$]undecane-3,7,10-trione, 1-hydroxy-1-germa-2,8,9-trithio-5-azatricyclo[3.3.3.0$^{1,5}$]undecane, 1-hydroxy-1-germa-2,8,9-trioxa-3-methyl-5-azatricyclo [3.3.3.0$^{1,5}$]undecane, 1-adamantyl-1-germa- 2,8,9-trioxa-5-azatricyclo[3.3.3.0$^{1,5}$]undecane, 1-adamantyl-1-germa-2,8, 9-trioxa-5-azatricyclo[3.3.3.0$^{1,5}$]undecane-3-one, 1-adamantyl-1-germa-2,8,9-trioxa-5-azatricyclo-[3.3.3.0$^{1,5}$] undecane-3,7-dione, etc.

All the known medicaments and biologically active compounds, which play an important role in vital activity of the human organism, form complexes with OGC, e. g., Antiviral medicaments: Midantanum, Remantadinum, Zidovodine (Retrovir), Virolex, Vidarabinum, Idoxuridine, Metisazonum, Oxolinum, Ganciclovir, Ribamidil;

Analgetic and antiinflammatory medicaments: acetylsalicylic acid, methylsalicylate, salicylamide, Mesalazine, Amidopyrinum, Analginum, Butadionum, Paracetamolum, Ibuprophenum, Naproxenum, Piroxicam, Sulindac, Dimexidum;

Antibacterial medicaments: Benzylpenicillinum-natrium, Oxacillinum-natrium, Ampicillinum, Cefaloridinum, Cefalexinum, Cefaclorum, Erythromycinum, Oleandomycini phosphas, Tetracyclinum, Oxytetracyclinum, Metacyclin, Laevomycetinum, Streptomycine sulfate, Neomycinum, Gentamycini sulfas, Sisomicini sulfas;

Sulfamide medicaments: Sulfadimezinum, Aethazolum, Urosulfanum, Sulphapyridazinum, Sulfadimethoxinum, Phtalazolum, etc.

Antituberculousis medicaments: Isoniacidum, Rifampicinum, Ethambutol, Ethionamide, Pirazinamide, Cycloserine, Florimicini sulfas;

Antitumor medicaments: Dopanum (Chlorethylaminouracil), Sarcolysinum (Racemelfalanum), Cyclophosphane, Chlorbutinum, Thiophosphamidum, Nitrosomethylurea, Myelosanum (Busulfan), Methotrexatum, Mercaptopurinum, Fluorouracil, Fluorofur, Dactinomycinum, Olivomycinum, Rubomycini hydrochloridum, Colchaminum, Vinblastine, Vincristine, Testosteroni propionas, Testoenatum, Synoestrolum, Phosphoestrolum, Aethyniloestradiolum, Hydrocortisonum, Prednisolone, Dexamethasonum, Triamcinolone, Cisplatin;

Antiepileptic medicaments: Phenobarbitalum, Diphenynum (Phenytoinum), Hexamidinum (Primidone), Sodium valproate, Lorazepam, Carbamazepin, Sibazonum (Diazepam), Trimethinum (Trimethadionum), Ethosuximidum;

Medicaments for Parkinson's syndrome: Levodopa, Cyclodolum, Mydocalm, Bromocryptinum, Carbidopa, Benserazide;

Psychotropic medicaments: Aminazinum, Meterazinum, Aethaperazinum, Chlorprotexenum, etc.

Tranquilizers: Diazepam, Mezapamum, Phenazepamum (Fenazepam);

Nootropic medicaments: Aminalonum, Pyracetamum;

Vitamins: A, $B_1$, $B_2$, $D_2$, $D_3$, E, $K_1$, $K_2$, PP, $B_5$, $B_6$, $B_{12}$, $B_c$, C, P;

Medicaments for treatment of schizophrenia: Aminazinum, Propazinum, Aethaperazinum;

Medicaments for treatment of cardiovascular system: Dibazolum, No-Spa, Papaverini hydrochloridum, Nitroglycerol, Erynitum, Validolum, Digitoxin, Celanidum, Quinidine Sulfate, Lidocaini hydrochloridum, Amiodaronum, Ornidum, Mesatonum, etc.

Aminoacids: glycine, alanine, valine, leucine, lysine, arginine, serine, cystine, etc.

Study of Reparative Effect of Medicaments and Biologically Active Substances Complexes with Organogermanium Compounds Usage of the complexes for local applications as liniments and ointments is favorable to speeding-up of wounds healing, betterment of morphologic and biochemical properties of the granulation-fibrous tissue in injuries. Content of nucleic acids, collagen, glycoproteids including hexuronic acid has considerably increased in the tissue. Intensive cellular proliferation (DNA) combined with high biosynthetic activity (RNA).

Implementation of the same compounds considerably cuts duration for knitting of fractures and cracks of bones. It turns out that implementation of the complexes is beneficial for prophylaxis and medical treatment of caries, what is connected to the reparative effect of the complexes. Depending on a kind of the complex duration of knitting reduced 1.3÷1.7 times compared to the control case.

Complexes of OGC with aminoacids, vitamins, medicaments for treatment of cardiovascular system, nootropic medicaments, analgesic and antiinflammatory ones, medicaments from other groups have been examined.

Investigation of Antihypoxic Properties of Medicament Complexes with Organogermanium Compounds Water solutions or suspensions of the complexes under investigation have been injected intraperitoneally 30÷60 min. before beginning of the experiment. Animals from the control group got equal amounts of physiological salt solution. High altitude hypoxia was made in special air tight chambers, in which a lift of the animals up to the altitude 10,000 m has been imitated by pumping out of air. A criterion of validity for the complexes was increase of mice life length and survivability of these. Individuals, which stayed alive at this altitude for more than 30 minutes and did not die after "lowering", were considered as survived ones. Organogermanium complexes with analgesic and antiinflammatory medicaments: acetylsalicylic acid, Paracetamolum, Amidopyrinum, etc., antiviral medicaments: Remantadinum, Midantanum, etc., antibiotics: Benzylpenicillinum natrium, Ampicillinum, Cephalexine, etc., aminoacids: glycine, alanine, valine, leucine, lysine, arginine, etc., medicaments for treatment of cardiovascular system: Dibazolum, No- -Spa, Methyldopa (Sandoz, Switzerland), Celanidum, Verapamilum, etc., and also medicaments belonging to other groups have been investigated. These complex compounds in doses 5÷20 mg/kg increased life lengths for animals 2÷4 times compared to animals from the control group and were on the level of a standard antihypoxic medicament—Mexaminum.

Interferon Inducing Activity of the Complexes of Medicaments and Biologically Active Compounds with Organogermanium Compounds Interferon inducing activity of the complexes has been studied with various methods, including the study with native leukocytes of human donor blood. The complexes were stimulatory to interferon production, activity of which in tests made up 1000÷2000 IU. It is pertinent to note that for Interferon inducing compounds, which are known nowadays, this value makes up in average 500÷2000 IU.

Complexes of OGC with aminoacids, vitamins, medicaments for treatment of cardiovascular diseases, nootropic medicaments, analgetics and antiinflammatory medicaments, antibiotics and medicaments from other groups have been studied.

Investigation of Antiinflammatory Properties of Complexes of Medicaments and Biologically Active Compounds with Organogermanium Compounds Antiinflammatory effect of complexes of medicaments and biologically active compounds with OGC has been studied by various methods including carrying out of clinical tests of ointments for contusions, strains and various inflammations.

Antiinflammatory effect has been studied for animals according to the method by Ju. Strel'nikov. Experiments have been carried out with white mice of mass 20 g. Aseptic inflammation was caused by injection of 0.1 ml of 2.5% formalin solution into thigh thickness of an animal's paw. A compound under investigation was injected into the stomach in the dose equimolecular to 20 mg/kg of indometacin two hours before the injection of formalin. Distinction of the edema was estimated by increase of a mass of inflamed and uninflammed paws in experimental groups of animals compared to control ones. Control animals were mice which did not get the compounds under investigation. Simultaneously antiinflammatory activity of indometacin was studied for comparison. Realized pharmacological studies have shown that the complexes cause reduction of the edema depending on a kind of a medicament and OGC from 40 up to 70% compared to the control group. Indometacin reduced the edema by 33.4%.

Complexes of OGC with aminoacids, vitamins, medicaments for treatment of cardiovascular diseases, nootropic medicaments, analgetics and antiinflammatory medicaments, antibiotics and medicaments from other groups have been studied.

Nootropic properties have been studied using common procedures [1].

Decrease of toxic effects of the complexes of medicaments with OGC was studied for animals and also estimated when carrying out clinical investigations compared to the individual medicament. The following factors were under estimation:decrease of acute toxicity ($LD_{50}$), decrease of side effect with non-allergic nature making up the spectrum of pharmacological effects for the medicament, decrease of side effect with allergic nature. Decrease of idiosyncrasy effects was also under estimation. Decrease of mutagenous, teratogenous and embryotoxic properties also was studied for the medicaments, which possess these side effects.

The complex toxicity of each individual medicament being considered as equal to 1, the toxicity of each complex medicament with OGC amounted to 0.15–0.6, depending on the kind of medicament and the kind of OGC.

Decrease of development of psychic and physical drug dependence also was estimated under implementation of a medicament with OGC compared to implementation of an individual medicament.

Taking into account expansion of therapeutic effect spectrum and increase of the main therapeutic effect, the total therapeutic index of a complex medicament increases by 3 to 5 times depending on the type of medicament and the kind of disease.

BRIEF DESCRIPTION OF FIGURES AND DRAWINGS

A scheme of effect of a medicament and a complex of the medicament with OGC is shown on FIG. 1.

A diagram for development of the AIDS disease is shown on FIG. 2.

The diagram of FIG. 1 schematically illustrates the effects of this invention. The therapeutic effects T are illustrated above the horizontal line and the adverse effects A below the horizontal line.

Zones 1 and 2 concern a known medicament used alone. It has an amount of therapeutic effect 1 over a given disease and an amount of adverse effects 2.

The right part of FIG. 1 concerns the complex according to the invention, of an OGC with the same medicament. Over said given disease the considerably increased therapeutic efficiency is illustrated by zones 3, and the adverse effects 4 are reduced. Moreover other therapeutic effects 6a (antihypoxic effect), 6b (Immunopotentiating effect), 6c (anti inflammatory effect), 6d (Reparative effect) and 6e (Nootropic effect) appear. All the zones marked with a cross correspond to therapeutic improvement due to the invention. Further description of this figure appears at a further stage of this description.

In FIG. 2, the horizontal axis is the time axis t. The curve 7 illustrates the virus development over time, with a strong initial peak 8, then a decrease due to immunitary defense, and again an increase leading to the letal phase. The curve 11 illustrates the corresponding phases of the immunitary defense. A first dotted curve 12 shows the effect of the complex according to the ivention if taken by the patient a short time after infection. The infection disappears after the peak. Dotted curves 13 and 14 show how the disease development and the immunitary defense are favourably affected by the complex taken a long time after infection. The letal phase is avoided or considerably delayed. Further description of the figure is given below.

VARIANTS FOR REALIZATION OF THE INVENTION

Toxicological properties of the organogermanium part of the complex medicaments are such that all the studied compounds are not toxic or low toxic ones. Acute toxicity of such compounds for white mice under the intragastric injection has made up ($LD_{50}$, mg/kg): R=hydroxyl—8400, $CH_3$— 7000, $C_2H_5$—8000, adamantyl>5000. Under the intragastric injection of these medicaments we failed to study parameters of acute toxicity of the medicaments for animals owing to impossibility of injecting so high doses into the stomach. Because the medicament in the dose 20.000 mg/kg has not caused any clinical effect and death of animals, based on trice-repeated study we assume by convention 20.000 mg/kg as $LD_{50}$. Cumulative properties are studied and it has been found that a cumulation rate of the medicament makes up a value more than 10. According to the classification of chemical compounds by the cumulation rate the medicament belongs to compounds which do not cumulate in organisms of animals.

Investigations of nervous system functional conditions were carried out according to change of a summary-liminal index and behavioral effects, the state of cardiovascular and respiratory systems by change of arterial pressure, pulse rate, respiration rate, condition of the kidneys was studied according to change of protein content in urine and diuresis, condition of the liver was studied according to change of protein content in blood and also composition of peripheric blood carried out in a subacute experiment with rats.

Histologic investigations of internal organs of animals under the experiment have been also carried out at the end of the experiment. It was shown that multiple injection of OGC to animals under the experiment in the dose 20.000 mg/kg does not cause any defect in functions of the nervous and cardiovascular systems, condition of the liver, the kidneys, the heart, the spleen, the stomach, the bowel and also changes in blood.

In the acute experiment under single and multiple exposures of the medicament on rat skin during three weeks it has been found that after the end of exposure and before repeated application of the medicament the skin fold thickness is not changed both under single and repeated exposures and tactile sense is retained. The medicaments under investigation did not possess mutagenous, teratogenous and embryotoxic properties.

The invention is confirmed by examples of specific application of the complexes of OGC with medicaments for treatment of various diseases.

Viral Diseases

OGC form complexes with all the known antiviral medicaments belonging to derivatives of adamantan (Midantanum, Remantadinum), to analogs of nucleosides (Zidovodine (Retrovir), Virolex, Ganciclovir, Vidarabinum, Idoxuridine, Metisazonum, Oxolinum, Ribamidil), etc.

Spectrum of therapeutic effect and antiviral effect expand under simultaneous decrease of medicaments toxicity and decrease of side effects (Tables 3 and 4).

Herpetic Infections

Quantitative determination of increase of therapeutic effect index for an antiherpetic medicament Virolex on the model of herpes genitalis for males of guinea pigs.

VIRUSES. The virus of herpes simplex (VHS) of the 2-nd antigenic type was implied in this work. Clinical symptoms of experimental herpes genitalis were registered daily before carrying out of treatment and were followed during the course of the disease.

The following parameters were used as criteria of infectious process danger: square and specific damage rate—presence of an edema, hyperemia, orchitis. Maximum distinction of each symptom made up 4 points. The present symptoms allow to buildup a scale and to express the course of the disease for each group under investigation from beginning of appearance of the first symptoms of the disease up to full disappearance of these. In this case index of therapeutic effect (ITE) is expressed with the following formula:

$$ITE\ (\%) = \frac{Q_c - Q}{Q_c},$$

where $Q_c$: sum of points in the control group of animals,

Q: sum of points in the group of animals which get the medicament.

The medicament, which is the complex of 1-hydroxy-1-germa-2,8,9-trioxy-5-azatricyclo[3.3.3.0$^{1,5}$]undecane with Virolex, in the form of films was inserted into animal's mouths and left on the muscous membrane of the mouth until these will be completely dissolved.

Treatment was began 48 hours after infecting when symptoms of the disease were distinct enough.

Description of Groups Under Investigation

The first group included animals infected with VHS-2 and not subjected to treatment with any medicament.

The second group included animals infected with VHS-2 and subjected to treatment with 5 mg of Virolex once a day.

The third group included animals infected with VHS-2 and subjected to treatment with 5 mg of Virolex complex with OGC once a day.

Results of Investigations

The first symptoms of the infection are a small edema and separate vesicles. These appear on the place of infecting 24–48 hours later. During the following days the clinical symptoms achieved their maximum: pastous elements coalesced, forming bloody anabrosis with symptom of orchitis. Then the infection calmed down and 11–17 days later the animals were practically convalescent.

TABLE 3

Efficiency of Medicaments with Experimental Herpes of Guinea Pigs

| Group of Animals # | Medicament, Dosage | Duration of the Disease Days | Total Index of Symptoms Distinction Points | Index of Therapeutic Effect (ITE) % |
|---|---|---|---|---|
| 1 | Control | 14,8 ± 3,2 | 50,0 | — |
| 2 | Virolex, 5 mg once a day | 11,1 ± 2,01 | 31,0 | 58 |
| 3 | Complex Virolex OGC 5 mg once a day | 6,2 ± 1,8 | 16,0 | 88,4 |

Implementation of Virolex: in the dose 5 mg per one guinea pig once a day (the second group of animals) led to decrease of distinctive symptoms down to 21 points (P<0, 05) (See Table 3). Animals treated with the medicament, which is a complex of Virolex with OGC in the dose 5 mg once a day were convalescent on sixth day after infecting, or 4.9 days earlier than in the second group. Distinctive clinical symptoms of the infectious process differed from the symptoms in the second group even next day or the third one after beginning of application of the present complex and made up 16.0 points, what is 15 points less than in the second group. Thus, the index of therapeutic effect for the complex exceeds by 1.9 times the index of therapeutic effect for Virolex. It also has been found that application of Virolex as the complex with OGC decreased its toxic effect on infected animals compared to pure Virolex (See Table 4).

Treatment of Common Cold and Influenza

Prescription of the medicament complexes with OGC (L OGC) in the predromal period of an acute respiratory disease has caused a considerable influence on development and course of the disease (See Table 4). The main symptoms (high temperature, weakness, cough, headache) were becoming less distinctive, duration of the disease decreased, an amount of complications sharply decreased compared to application of individual medicaments. Taking L.OGC during the influenza has led not only to slackening of the main symptoms of the disease and considerable decrease of after-effects of the influenza, but also to forming of a stable immunity against the flue (during 5 years of observation any case of influenza has not been found). It is possible that the flue took place, but its symptoms were so slackened that these were not different from the common cold. The disease lasted 1–2 days and it was connected to an insignificant increase of temperature. Grease of nasal cavities with ointments containing complexes of OGC with medicaments and biologically active compounds at the beginning of the common cold and in the case of a nasal cold, as a rule, prevented and stopped development of the disease and the nasal cold.

Treatment of AIDS and Opportunistic Infections with AIDS

Proposed complexes of OGC with medicaments are used in therapy of AIDS and opportunistic infections with AIDS on the background of common therapy.

Therapeutic effect of Zidovudine (Retrovir) is revealed mainly during the first 6–8 months after beginning of the therapy. Zidovudine mainly does not cure patients, but only delays development of the disease. Besides, medicamentous stability of retroviruses develops to the medicament. Among side effects of Zidovudine the first place is taken by hematological breaches: anemia, neutropenia, trombocytopenia. Headache, insomnia, myalgia and suppression of kidneys functions are also possible.

Let us consider a diagram (FIG. 2) of typical development of AIDS, published in an article by Robert R. Redfield et al. [12]. On the authors' hypotetis, equilibrium between HIV and immune system gradually displaces. The diagram shows a typical picture of development of the disease. During the first period after infection a quantity of viral particles in the organism sharply increases up to peak 8, then immune response is developed. During some time, usually for several years, the immune system (curve 11) still functions normally and restrains reproduction of the virus. However the virus is gradually disseminated in the organism and there comes a point where scale moves to the side of the virus and the immune system disappears. Treatment for AIDS has been carried out on the background of an AIDS therapy accepted at present time based on Zidovudine. The treatment according to this example of the invention, includes application of the complex of Zidovudine with OGC and its derivatives or other medicaments and active therapy of opportunistic diseases.

Therapeutic picture of treatment for AIDS considerably changes. Efficiency of treatment for AIDS substantially increases, stability of the retrovirus to medicaments does not develop or develops slowly. Side effects sharply decrease, which are usually observed under usage of Zidovudine and other medicaments. A picture of treatment for AIDS using a complex of Zidovudine with OGC on the background of the common AIDS therapy is presented in FIG. 2 (dotted lines 12, 13, 14).

The AIDS virus-pathogene can directly injure organs and tissues, but in addition to it, undermining protective forces of the organism, it prepares the soil for development of opportunistic infections, i. e., diseases caused by pathogens, intensive reproduction of which in the patient's organism is possible in connection to the injury of the immune system [13]. It is found that development of some specific opportunistic infections is connected to an amount of T-lymphocytes in blood, possessing $CD_4$. The first infectious diseases appear when one milliliter of blood contains less than 200–400 helper lymphocytes [13].

Usage of OGC complexes with medicaments applied in therapy of opportunistic infections with AIDS has become an effective therapeutic method and gives the following results: prevention of infections development, contribution to prevention of relapses (secondary prophylaxis).

Usage of Zidovudine complexes in combination with OGC leads to decrease of a probability of hematological breaches: neutropenia, trombocytopenia. Such side effects as headache, insomnia, myalgia and suppression of kidneys functions decrease with considerable increase of efficiency of the complex medicament (See Table 4).

Treatment of Severe Chronic Neurologic Diseases of Central and Vegetative Nervous System The peculiarities of such diseases are severe course, early disablement, low efficiency of traditional medicaments. In most cases, usage of medicament complexes with OGC led to improvement of general condition, abatement of the main symptoms of the disease, normalization of broken functions and even lost ones.

Alzheimer Disease and Senile Changes in Brain

Neuropathic changes have shown that in many developed countries the most common causes of senile dementia are abnormal formations in brain, such as senile patches and neurofibrillar glomes first described by a Bavarian psychiatrist Aloys Alzheimer in 1907 [14]. Although genetic background of the Alzheimer disease is obvious, nontheless, a mechanism of pathologic changes development in brain is not quite clear. Moreover, amyloid deposits and neurofibrillar glomes are typical not only for the Alzheimer disease, these can be met under no less than ten chronic diseases of the human brain.

Many people at the age of around 80 years old have at least several senile patches and neurofibrillar glomes, particularly in the hypocamp and in other areas of brain, which are important for memory. Mainly a difference between normal senescence and the Alzheimer disease is more likely to be quantitative, than qualitative. Mainly under progressive dementia following the pattern seen in the Alzheimer disease more mature patches and neurofibrillar glomes are observed in more or less amount (sometimes considerable one) than normal elderly people have [14].

Thus, prevention or considerable deceleration of senile patches and neurofibrillar glomes formation is a key to therapy of various diseases of human brain and to prolongation of active human lives.

Prophylaxis and treatment of a complex of human brain diseases including the Alzheimer disease and also prolongation of active period of human lives reside in peroral or injection application of the complexes of OGC with medicaments.

Application of such complexes stops or considerably delays formation of senile patches and neurofibrillar glomes and thus prevents development of human brain diseases, including the Alzheimer disease.

Usage of OGC complexes with medicaments in a late development stage of the disease delays the disease development and leads to partial remission.

It has been found that under the Alzheimer disease it is efficient to imply complexes of medicaments-aminoacids (glycine, alanine, valine, leucine, lysine, arginine, serine, etc.), nootropic medicaments (Pyracetamum, Aminalonum), antiviral medicaments (Remantadinum, Midantanum, etc.), medicaments for treatment of cardiovascular system (Dibazolum, No-Spa, etc.), antiinflammatory medicaments (acetylsalicylic acid, Indometacinum), tranquilizers (Phenazepamum, Diazepam) and also medicaments with OGC which belong to other groups. The following compounds are applied as the organogermanium part of the complex:

1-hydroxy-1-germa-2,8,9-trioxa-5-azatricyclo[$3.3.3.0^{1,5}$] undecane,
1-thiohydroxy-1-germa-2,8,9-trioxa-5-azatricyclo[$3.3.3.0^{1,5}$]undecane,
1-methyl-1-germa-2,8,9-trioxa-5-azatricyclo[$3.3.3.0^{1,5}$] undecane-3-one,
1-adamantyl-1-germa-2,8,9-trioxa-5-azatricyclo-[$3.3.3.0^{1,5}$] undecane-3,7-dione,
1-hydroxy-1-germa-2,8,9-trithio-5-azatricyclo[$3.3.3.0^{1,5}$] undecane, etc.

Complexes of OGC with medicaments are also efficient for other severe diseases of central and vegetative nervous system. E. g., in the cases of multiple sclerosis, epilepsy, diabetic polyneuritis, toxic polyneuritis, brain circulatory disturbance, prophylaxis of insults, in the postinsult period and also under other diseases (See Table 5).

Complexes of OGC with medicaments are a strong remedy for prophylaxis of all the mentioned neurologic diseases.

Application of Organogermanium Compounds Jointly with Tranquilizers

Complexes of OGC with tranquilizers (Diazepam, Mezapamum, Phenazepamum, etc.) possess wider complex of activity compared to initial tranquilizers. Complexes of OGC with tranquilizers have shown antiinflammatory properties, antihypoxic, immunostimulating, repairing and nootropic effects. It turned out that the complex medicaments are more efficient compared to initial tranquilizers concerning decrease of insomnia, suppression of phobia, anxiety, agitation, tensity.

Organogermanium compounds increase efficiency of tranquilizers application in all the spectrum of their effect. Efficiency of tranquilizers application for decrease of phobia, anxiety, agitation, tensity has increased. Efficiency of tranquilizers also has increased for treatment of various mental diseases and marginal states, e. g., schizophrenia with neurosoidal symptomatology, depressive and hypochondriacal states, for cutting abstinence syndrome under alcoholism and for treatment of other diseases.

Application of the OGC complexes with tranquilizers gives a possibility to decrease an efficient dose of tranquilizer application and to slacken side effects under application of these in a considerable extent: quickness of mental and physical reaction practically does not decrease, working capacity does not decrease, sleepiness and head ache slacken, decrease of sexual potency is not observed, skin injuries and other side effects typical for application of tranquilizers do not appear. Possibilities of physical and mental habituation decrease. The following compounds are applied as the organogermanium part of the complex:

1-hydroxy-1-germa-2,8,9-trioxa-5-azatricyclo[$3.3.3.0^{1,5}$] undecane,
1-adamantyl-1-germa-2,8,9-trioxa-5-azatricyclo-[$3.3.3.0^{1,5}$] undecane-3,7-dione,
1-thiohydroxy-1-germa-2,8,9-trioxa-5-azatricyclo[$3.3.3.0^{1,5}$]undecane, etc.

Oncologic Diseases

One of limiting moments in medicamentous therapy of malignant tumors is habituation of tumoral cells to medicaments. A process of such habituation can be retarded to some degree through combined application of medicaments which have different structure and unequal mechanism of effect [1].

Moreover, a considerable shortcoming of modern medicaments is low discrimination of effect related to tumoral cells. Usually application of antitumor medicaments is accompanied by serious side effects and toxic ones. In such cases actively proliferating tissues (bone marrow, muscous membrane of the intestine) suffer most of all. Many medicaments cause suppressive influence on functions of sexual glands. A number of antibiotics with antitumor activity possess cardiotoxic effect. Antiblastic medicaments also possess immunodepressive, mutagenous and teratogenous effects [1].

Usage of OGC complexes with antitumor medicaments allows sharply to increase efficiency of malignant tumors treatment with considerable decrease of their toxic influence on the organism. There has been found an effect of habituation absence or habituation delay of cancer cells to the chemical medicaments.

Sharp decrease of the complex antitumor medicaments toxic influence on the organism allows to vary dosage of these in a wide range, obliterating cancer cells with high level of probability and achieving in many cases full healing. OGC complexes with medicaments were prescribed to patients with the third and the fourth stages of cancer of the mammary gland, the larynx, the straight intestine, sarcoma of chest tissues, the sheath, the stomach, the urinary bladder, the liver, the meningis, bone tissues, the prostate, etc. Complexes of medicaments with OGC are valuable when surgical ablation of the tumor and radiotherapy. The following compounds are applied as the organogermanium part of the complex:

1-hydroxy-1-germa-2,8,9-trioxa-5-azatricyclo[$3.3.3.0^{1,5}$] undecane,
1-thiohydroxy-1-germa-2,8,9-trioxa-5-azatricyclo[$3.3.3.0^{1,5}$]undecane,
1-hydroxy-1-germa-2,8,9-trioxa-5-azatricyclo[$3.3.3.0^{1,5}$] undecane-3-one,
1-adamantyl-1-germa-2,8,9-trioxa-5-azatricyclo-[$3.3.3.0^{1,5}$] undecane-3,7-dione, etc.

The following antitumor medicaments are applied as a medicament part of the complexes: Dopanum (Chlorethylaminouracil), Sarcolysinum (Racemelfalanum), Cyclophosphane, Chlorbutinum, Thiophosphamidum, Nitrosomethylurea, Myelosanum (Busulfan), Methotrexatum, Mercaptopurinum, Fluorouracil, Fluorofur, Dactinomycinum, Olivomycinum, Rubomycini hydrochloridum, Colchaminum, Vinblastine, Vincristine, Testosteroni propionas, Testoenatum, Synoestrolum, Phosphoestrolum, Aethyniloestradiolum, Hydrocortisonum, Prednisolone, Dexamethasonum, Triamcinolone, Cisplatin, etc.

Practically all the patients manifested a positive reaction on application of the OGC complexes with the medicaments. Their general state was getting better, progressing of the oncological process delayed, remission of the oncological process was observed, indices of peripheric blood were improved. Intoxication phenomena were considerably decreased. Toxic influence on actively proliferating tissues (bone marrow, muscous membrane of the intestine) was decreased. Suppressive influence on sexual glands was decreased. Immunodepressive, mutagenous and teratogenous effects were decreased compared to the original medicament. An estimate of general toxic effect of complex antitumor medicaments with OGC only amounts to 0.15–0.3, if the toxicity of the individual medicament is considered as being equal to 1. With the aim of cancer diseases prevention one can apply complexes of OGC with organism tonic preparations (aminoacids, vitamins, etc.)

Treatment of Cardiovascular Diseases

Application of the complexes of medicaments with OGC for treatment of cardiovascular diseases gives a considerable positive effect compared to usage of initial medicaments. The main pharmaceutical effect of the medicament was accompanied with appearance or considerable increase of antiinflammatory properties, antihypoxic effect, immunopotentiating effect, repairing and nootropic effects. The main pharmacological effect also increased. Total therapeutic effect index with taking into account therapeutic effects spectrum expansion for the complex medicament and increase of the main therapeutic effect increased depending on the kind of medicament and the type of disease 3–4 times.

As a result of the above mentioned facts efficiency of cardiovascular diseases treatment is considerably increased.

The complexes are efficient for prevention of infarcts and unexpected deaths and also in postinfarct therapy. Endurance to medicaments was improved and negative effect of traditional therapy on the organism decreased.

The following medicaments have been applied as a medicament part of the complexes: Dibazolum, No-Spa, Papaverini hydrochloridum, Nitroglycerol, Erynitum, Validolum, Digitoxin, Celanidum, Quinidine Sulfate, Lidocaini hydrochloridum, Amiodaronum, Ornidum, Mesatonum, etc.

The following compounds have been applied as the organo germanium part of the complex:
1-hydroxy-1-germa-2,8,9-trioxa-5-azatricyclo[$3.3.3.0^{1,5}$] undecane,
1-thiohydroxy-1-germa-2,8,9-trioxa-5-azatricyclo[$3.3.3.0^{1,5}$]undecane,
1-methyl-1-germa-2,8,9-trioxa-5-azatricyclo[$3.3.3.0^{1,5}$] undecane-3-one,
1-methyl-1-germa-2,8,9-trioxa-5-azatricyclo-[$3.3.3.0^{1,5}$] undecane-3,7-dione,
1-adamantyl-1-germa-2,8,9-trioxa-5-azatricyclo-[$3.3.3.0^{1,5}$] undecane-3,7-dione,
1-hydroxy-1-germa-2,8,9-trithyo-5-azatricyclo[$3.3.3.0^{1,5}$] undecane,
1-adamantyl-1-germa-2,8,9-trioxa-5-azatricyclo-[$3.3.3.0^{1,5}$] undecane-3-one, etc.

Application of Complexes of Organogermanium Compounds with Analgetics and Antiinflammatory Medicaments Application of the OGC complexes with analgetics and antiinflammatory medicaments—acetylsalicylic acid, methylsalicylate, salicylamide, Mesalazine, Paracetamolum, Amidopyrinum, Analginum, Butadionum, Indometacin, Brufen (Ibuprofenum), Pyrogenalum, Sulindac, Dimexidum, Naproxenum—demonstrates a considerable positive effect compared to usage of the original medicaments. Spectrum of the complex medicaments effect is expanded (antihypoxic effect, immunopotentiating one, repairing and nootropic effects). Antiinflammatory effect of the complex medicaments sharply increases, analgetic effect also increases.

Total therapeutic effect index with taking into account therapeutic effects spectrum expansion for the complex medicament and increase of the main therapeutic effect increased 3–4 times depending on the kind of medicament and the type of disease.

Side effects of analgetics and antiinflammatory medicaments were considerably decreased. Dyspeptic disfunctions (nausea, vomiting, diarrhea, gastric hemorrhage) and allergic reactions were decreased. Probability of serious disfunctions from the side of hemipoietic organs (agranulocytosis, aplastic anemia) and the liver was considerably decreased.

An estimate of total toxic effect of the complex medicaments, containing OGC, has only amounted to 0.3–0.4, if the toxicity of an individual medicament is considered as being equal to 1.

The following compounds have been applied as the organo germanium part of the complex:
1-hydroxy-1-germa-2,8,9-trioxa-5-azatricyclo[$3.3.3.0^{1,5}$] undecane,
1-ethyl-1-germa-2,8,9-trioxa-5-azatricyclo[$3.3.3.0^{1,5}$] undecane-3-one,
1-ethyl-1-germa-2,8,9-trioxa-5-azatricyclo[$3.3.3.0^{1,5}$] undecane-3,7-dione,
1-hydroxy-1-germa-2,8,9-trithyo-5-azatricyclo-[$3.3.3.0^{1,5}$] undecane, etc.

Application of Complexes of Organogermanium Compounds with Antibiotics and Sulfamides Application of the OGC complexes with antibiotics is noted for its increased efficiency compared to initial medicaments. It is also found that the complex medicaments are characterized by an expanded spectrum of their effects. Besides their antimicrobic effect, the medicaments cause antiinflammatory, antihypoxic, immunopotentiating, reparative and nootropic effects. Antimicrobic activity of antibiotics increases, including antituberculosis medicaments. Allergic reactions of immediate and delayed types (serum sickness, angioneurotic edema, anaphylactic shock, contact dermatitises) decrease. Non-allergic side effects and toxic effects decrease. Dyspeptic disfunctions (nausea, vomiting, diarrhea), painfulness at the place of the complex medicament intramuscular injection, development of phlebitises and trombophlebitises after intravenous injections are decreased, as well as unfavorable effects for the liver, the kidneys, the hemopoietic organs, organs of audition, etc. Usage of the OGC complexes with antibiotics is of particular efficiency for prevention of superinfection (disbacteriosis) development.

An estimate of total toxic effect of antibiotic complexes with OGC has only amounted to 0.3–0.4, if toxicity of individual medicaments is considered as being equal to 1.

Antibiotics of various groups have been used as the medicament part of the complexes: Benzylpenicillinum-natrium, Oxacillinum-natrium, Ampicillinum, Cefaloridinum, Cefaclorum, Erythromycinum, Oleandomycini phosphas, Tetra-cyclinum, Metacyclin, Laevomycetinum, Streptomycin sulfate, Neomycinum, Gentamycini sulfas, Sisomicini sulfas, Cycloserine, Kanamycini sulfas, Florimycini sulfas.

The same compounds have been applied as the organogermanium part of the complexes as mentioned in the Section "Treatment for Cardiovascular Diseases". Similar results were obtained when investigating the complexes of sulfamide medicaments (Sulfadimezinum, Aethazolum, Urosulfanum, Sulphapyridazinum, Sulfadimethoxinum, Phtalazolum, etc.) with OGC.

Prophylaxis and Treatment of Paradontosis and Caries

Tooth pastes, other compositions and food additives containing the OGC complexes of antibacterial medicaments, vitamins, aminoacids, fluoride compounds and medical herbs tinctures are applied for treatment of oral cavity diseases, above all else paradontosis and caries.

In doing so the effects spectrum of antibacterial medicaments, vitamins, aminoacids, fluoride compounds and medical herbs tinctures expands. Antiinflammatory, antihypoxic, immunopotentiating, repairing effects appear or considerably increase with the OGC complexes.

Efficiency of the complexes for prophylaxis of caries is possibly connected to repairing effect of these, which is observed during treatment of traumatic and pathologic fractures as well as bone cracks.

The same compounds have been applied as the organogermanium part of the complexes as mentioned in the Section "Treatment for Cardiovascular Diseases".

Treatment of Traumatic and Pathologic Fractures as well as Bone Cracks

The OGC complexes of aminoacids, vitamins, ATP and medical herbs tinctures are applied for speeding-up of bone tissue adhesion under traumatic and pathologic fractures as well as bone cracks. In doing so the effects spectrum of the complex medicaments expands compared to initial ones. Repairing, antiinflammatory and immunopotentiating effects appear or considerably increase with the OGC complexes.

Periods for adhesion of fractures and bone cracks are considerably reduced compared to usage of initial medicaments. Depending on the kind of fracture and the type of the applied complex a period of adhesion of a fracture or a bone crack is reduced 1.3–1.7 times.

The same compounds have been applied as the organogermanium part of the complexes as mentioned in the Section "Treatment for Cardiovascular Diseases".

Application of the OGC Complexes of Medicaments and Biologically Active Compounds in Therapy of Narkomania, Decrease of Mental and Physical Drug Dependence, Habituation and Reduction of Abstinence Syndrome The OGC complexes of aminoacids, vitamins, nootropic medicaments and benzodiazepines are applied in therapy of narkomania caused by morphine derivatives, barbiturates and other compounds for decrease of physical drug dependence, habituation and reduction of abstinence syndrome.

Owing to formation of the OGC complexes the effects spectrum of medicaments and biologically active compounds is expanded. The complex medicaments exhibit antitoxic, reparative, antiinflammatory, immunopotentiating and nootropic effects. These complexes are found to be efficient for treatment of various types of narcomania and drug dependence. Periods of abstinence syndrome manifestation and treatment are reduced.

The same compounds have been applied as the organogermanium part of the complexes as mentioned in the Section "Treatment for Cardiovascular Diseases".

Application of the OGC Complexes of Medicaments and Biologically Active Compounds as Food Additives The complexes of OGC with organism tonic preparations, medicaments, vitamins, aminoacids, ferments, carbohydrates and other biologically active compounds with OGC have passed tests as food additives to all the kinds of food products for various strata of population.

The same compounds have been applied as the organogermanium part of the complexes as mentioned in the Section "Treatment for Cardiovascular Diseases".

Owing to formation of the complexes with germanium the effects spectra of organism tonic preparations, vitamins, aminoacids, ferments, carbohydrates and other biologically active compounds were expanded. Antiinflammatory, antihypoxic, immunopotentiating, repairing and nootropic effects appear or considerably increase for the OGC complexes.

Social groups of population having active life style connected to heavy mental and emotional loads—business-men, persons of creative professions, scientists, sportsmen point out improvement of general state, increase of creative and general efficiency.

Elder social groups of population and persons, who live in areas with unfavorable ecology, including territories contaminated with radiation, and also employees, which are busy in branches of industry with heavy and harmful working conditions pointed out improvement of their general state, decrease of total morbidity including cases of common cold and influenza, increase of general working efficiency.

Application of the OGC Complexes of Medicaments and Biologically Active Compounds in Cosmetics and Therapeutic Cosmetics The OGC complexes of medicaments, vitamins, aminoacids, ferments, hormones, ATP, extracts and tinctures of medicinal plants (ginseng, aloe, yarrow, St. John's-wort, hop, nettle, camomile, burdock, calendula, coltsfoot, oak bark, etc.) are added to cosmetic remedies and therapeutic cosmetic ones.

The same compounds have been applied as the organogermanium part of the complexes as mentioned in the Section "Treatment for Cardiovascular Diseases".

Owing to formation of the OGC complexes the effects spectrum of initial cosmetic remedies and therapeutic cosmetic ones is expanded. Besides their main pharmacological effect the OGC complexes of cosmetic remedies and therapeutic cosmetic ones acquire or considerably increase their antiinflammatory, immunopotentiating and repairing effects. The main pharmacological effect of the remedies also increases. Their complex effect on human skin is characterized with increase of improving influence on the vascular system, regenerating, antiinflammatory, bactericidal and antiviral effects which lead to a considerable therapeutic and rejuvenascent effect.

The complex preparations are efficient remedies for prophylaxis and therapy of cellulite.

Individual intolerance and allergic reactions are serious problems in usage of cosmetic remedies and therapeutic cosmetic ones. The OGC complexes of cosmetic remedies and therapeutic cosmetic ones have a considerably decreased level of individual intolerance and probability for appearance of allergic reactions.

Industrial Application

Efficiency of implementation of the present method for expansion of therapeutic effect spectra, increase of therapeutic effect and decrease of medicaments toxicity are illustrated with data of the following Tables.

TABLE 4

Treatment of Viral Diseases using the OGC Medicaments Complexes, Expansion of their Therapeutic Effects Spectrum and Decrease of their Toxicity

| # | OGC Medicament Complex | Kind of Disease | Efficiency Increase * | Decrease of Medicament Toxic Effects** | Expansion of Effect Spectrum for the Complex Medicament*** |
|---|---|---|---|---|---|
| 1. | Virolex OGC | | | | |
| | OGC (R = OH) | Herpes | 1,9 | 0,4 | AI, AH, IP, R, N |
| | OGC (R = SH) | - . - | 1,8 | 0,4 | |
| | OGC (R = C$_2$H$_5$, R$_1$, R$_2$ = O) | - . - | 1,8 | 0,5 | - . - |
| 2. | Vidarabinum OGC | | | | |
| | OGC(R = OH) | Zocter encefalitis | 2,3 | 0,4 | - . - |
| | OGC(R = OH, R$_1$ = CH$_3$) | - . - | 2,2 | 0,5 | - . - |
| | OGC (R = OH, R$_1$,R$_2$ = O) | - . - | 2,2 | 0,4 | - . - |
| 3. | Idoxuridine OGC | | | | |
| | OGC (R = OH) | Keratitis | 2,1 | 0,4 | - . - |
| | OGC (R = SH) | - . - | 2,1 | 0,4 | - . - |
| | OGC (R = C$_2$H$_5$, R$_1$,R$_2$ = O) | - . - | 2,0 | 0,4 | - . - |
| 4. | Remantadinum OGC | | | | |
| | OGC (R = OH) | Influenza (prophylaxis /treatment, decrease of complications, forming of immunity) | 3,0 | 0,4 | AI, AH, IP, R, N |
| | OGC (R = OH, R$_1$R$_2$ = O) | - . - | 3,0 | 0,4 | - . - |
| | OGC (R = SH) | - . - | 3,0 | 0,4 | - . - |
| 5. | Midantanum OGC | | | | |
| | OGC (R = OH) | - . - | 2,8 | 0,5 | - . - |
| | OGC (R = CH$_3$, R$_1$R$_2$ = R$_5$R$_6$ = O) | - . - | 2,8 | 0,5 | - . - |
| | OGC (R = SH) | - . - | 2,7 | 0,5 | - . - |
| 6. | Dibasolum OGC | | | | |
| | OGC (R = OH) | - . - | 3,5 | 0,5 | - . - |
| | OGC (R = CH$_3$, R$_1$R$_2$ = R$_5$R$_6$ = O) | - . - | 3,0 | 0,6 | - . - |
| | OGC (R = SH) | - . - | 3,4 | 0,5 | - . - |

TABLE 4-continued

Treatment of Viral Diseases using the OGC Medicaments Complexes, Expansion of their Therapeutic Effects Spectrum and Decrease of their Toxicity

| # | OGC Medicament Complex | Kind of Disease | Efficiency Increase * | Decrease of Medicament Toxic Effects** | Expansion of Effect Spectrum for the Complex Medicament*** |
|---|---|---|---|---|---|
| 7. | Zidovudine OGC | | | | |
| | OGC (R = OH) | AIDS | 2,5 | 0,5 | - . - |
| | OGC (R = SH) | AIDS | 2,4 | 0,5 | - . - |
| | OGC (R = CH$_3$, R$_1$R$_2$ = R$_5$R$_6$ = O) | AIDS | 2,4 | 0,5 | - . - |
| | OGC (R = OSiMe$_3$) | AIDS | 2,5 | 0,5 | - . - |
| | OGC (R = OGeMe$_3$) | AIDS | 2,6 | 0,5 | - . - |

Total therapeutic effect, taking into account expansion of the spectrum of the complex medicament therapeutic effect and increase of the effect, increases 3 ÷ 5 times depending on the kind of medicament and the type of disease.
* Efficiency of the individual medicament is considered as being equal to 1.
**Toxic effects of the individual medicament are considered as being equal to 1.
***AI:Antiinflammatory effect, AH:antihypoxic effect, IP:immunopotentiating effect, R:reparative effect, N:nootropic effect.
1) The symbol "=" means "is constituted by"
2) Only those substituents in OGC of formula II which differ from hydrogen atoms are indicated.

TABLE 5

Treatment of Severe Chronic Nervous Diseases of the Central and Vegetative Nervous System using the OGC Medicaments Complexes. Expansion of Therapeutic Effects Spectrum and Decrease of Toxicity for the Complexes

| # | OGC Medicament Complex | Kind of Disease | Efficiency Increase * | Decrease of Medicament Toxic Effects** | Expansion of Effect Spectrum for the Complex Medicament*** |
|---|---|---|---|---|---|
| 1. | Phenobarbitalum OGC | | | | |
| | OGC(R = OH) | Epilepsy | 1,7 | 0,4 | AI1 AH, IP, R, N |
| | OGC(R = SH) | - . - | 1,8 | 0,5 | - . - |
| | OGC (R = adamantyl, R$_1$R$_2$ = R$_5$R$_6$ = O) | - . - | 2,5 | 0,4 | - . - |
| 2. | Dipheninum OGC | | | | |
| | OGC (R = OH) | - . - | 1,7 | 0,4 | - . - |
| | OGC (R = adamantyl, R$_1$R$_2$ = R$_5$R$_6$ = O) | - . - | 2,4 | 0,4 | - . - |
| 3. | Hexamidinum OGC | | | | |
| | OGC (R = OH) | - . - | 1,6 | 0,4 | - . - |
| | OGC (R = adamantyl, R$_1$R$_2$ = R$_5$R$_6$ = O) | - . - | 2,4 | 0,4 | - . - |
| 4. | Midantanum OGC | Parkinson's syndrome | | | |
| | OGC (R = OH) | - . - | 1,5 | 0,4 | - . - |
| | OGC (R = SH) | - . - | 1,6 | 0,4 | - . - |
| | OGC (R = adamantyl, R$_1$R$_2$ = R$_5$R$_6$ = O) | Parkinson's syndrome | 1,8 | 0,4 | AI, AH, IP, R, N |
| 5. | Levodopa OGC | | | | |
| | OGC (R = OH) | - . - | 1,5 | 0,3 | - . - |
| | OGC (R = adamantyl, R$_1$R$_2$ = R$_5$R$_6$ = O) | - . - | 1,8 | 0,3 | - . - |

TABLE 5-continued

Treatment of Severe Chronic Nervous Diseases of the Central and Vegetative Nervous System using the OGC Medicaments Complexes. Expansion of Therapeutic Effects Spectrum and Decrease of Toxicity for the Complexes

| # | OGC Medicament Complex | Kind of Disease | Efficiency Increase * | Decrease of Medicament Toxic Effects** | Expansion of Effect Spectrum for the Complex Medicament*** |
|---|---|---|---|---|---|
| 6. | Aminazinum OGC | | | | |
| | OGC (R = OH) | Disfunctions of human psychic activities | 1,8 | 0,3 | - . - |
| | OGC (R = SH) | - . - | 1,7 | 0,3 | - . - |
| | OGC (R = adamantyl, $R_1R_2 = R_5R_6 = O$) | - . - | 2,1 | 0,3 | - . - |
| 7. | Meterazinum OGC | | | | |
| | OGC (R = OH) | - . - | 1,7 | 0,3 | - . - |
| | OGC (R = SH) | - . - | 1,7 | 0,3 | - . - |
| | OGC (R = CH3, $R_1R_2 = R_5R_6 = O$) | - . - | 1,5 | 0,4 | - . - |
| 8. | Chlorprotexenum OGC | | | | |
| | OGC (R = OH) | - . - | 1,8 | 0,4 | - . - |
| | OGC (R = SH) | - . - | 1,7 | 0,4 | - . - |
| | OGC (R = $C_2H_5$, $R_1R_2 = R_5R_6 = O$) | - . - | 1,4 | 0,4 | - . - |
| 9. | Diazepam OGC | | | | |
| | OGC (R = OH) | Tranquilizer | 1,9 | 0,4 | - . - |
| | OGC (R = SH) | - . - | 1,8 | 0,4 | - . - |
| | OGC (R = adamantyl, $R_1R_2 = R_5R_6 = O$) | Tranquilizer | 2,5 | 0,4 | AI, AH, IP, R, N |
| 10. | Phenazepamum OGC | | | | |
| | OGC (R = OH) | - . - | 1,8 | 0,3 | - . - |
| | OGC (R = adamantyl, R1R2 = O) | - . - | 2,2 | 0,3 | - . - |
| | OGC (R = $CH_3$) $R_1R_2 = R_5R_6 = R_9R_{10} = O$) | - . - | 1,5 | 0,4 | - . - |
| 11. | Mezapamun OGC | | | | |
| | OGC (R = OH) | - . - | 1,8 | 0,3 | - . - |
| | OGC (R = adamantyl, $R_1R_2 = O$) | - . - | 2,1 | 0,3 | - . - |
| | OGC (R = $CH_3$) $R_1R_2 = R_5R_6 = O$) | - . - | 1,4 | 0,4 | - . - |
| | OGC (R = $OSiMe_3$) | - . - | 1,5 | 0,4 | - . - |
| | OGC (R = $OGeMe_3$) | - . - | 1,9 | 0,4 | - . - |

Total therapeutic effect, taking into account expansion of the spectrum of the complex medicament therapeutic effect and increase of the effect, increases 3 ÷ 5 times depending on the kind of medicament and the type of disease.
* Efficiency of the individual medicament is considered as being equal to 1.
**Toxic effects of the individual medicament are considered as being equal to 1.
***AI:Antiinflammatory effect, AH:antihypoxic effect, IP:immunopotentiating effect, R:reparative effect, N:nootropic effect.
1) The symbol "=" means "is constituted by"
2) Only those substituents in OGC of formula II which differ from hydrogen atoms are indicated.

REFERENCES

1. Kharkevich. A. Pharmacology—I.: Meditsina, 1993.—543 p. (Rus.)
2. Lukevits E. Ya., Gar T. K., Ignatovich L. M., Mironov V. F. Biological Activity of Organogermanium Compounds: Riga: Zinatne, 1990.—191 p. (Rus.)
3. Asai K. Miracle Cure: Organic Germanium—Tokyo: Jpn. Publ. Inc., 1980.—171 p.
4. Asai K. Organic Germanium: a Medical God Send—Tokyo: Kogakusha Ltd, 1977.—154 p.
5. Sato H., Iwagychi T. Antitumor Activity of New Organogermanium Compound Ge-132//Gan no Rinsho, Nippon, 1979, vol. 6, $^1$1, p. 79–83.
6. Kakimoto N. Organogermanium Sesquioxide: Pat. 55–81890, Jpn., 1980//C.A., 1981, vol. 94, ref. 84305e.
7. Suzuki F., Pollard R. B. Prevention of Suppressed Interferon Gamma Production in Thermally Injured Mice by Administration of a Novel Organogermanium Compound Ge-132//J. Interferon Res., 1984, vol. 4, $^1$2, p. 223–233.
8. Aso H., Suzuki T., Ebina T., Ishida N. Antiviral Activity of Carboethoxygermanium-sesquioxide (Ge-132) in Mice Infected with Influenza Virus//J. Biol. Response Modif., 1989, vol. 8, p. 180.
9. Savai K., Kurono M., Sano K., Mitam T. et al. Use of a Composition Containing Organic Germanium for Treating AIDS and in the Production of Interferon: Eur. Pat. 360776 (Cl A61R33/24), May 23, 1990.
10. Sawai K., Kurono M., Awaya I. et al. Composition Containing Organogermanium Compound and Immunity Adjusting Composing the Composition: U.S. Pat. No. 5,340,806 (Kl. 514–184), Aug. 23, 1994.
11. Cato T. Organic Germanium Polymers as Therapeutic Agents: Pat. 55-167222 Jpn. (1980)//C. A., 1981, vol. 94, ref. 185729 b.
12. Redfield R. R., Berke D. S. Clinical Picture of Infection with AIDS Virus//V Mire Nauki, [1]12, 1988, p. 60–69 (Scientific American, October 1988, vol. 259, [1]4). (Rus.)
13. Mills J., Mazur G., Infections Connected to AIDS//V Mire Nauki, [1]10, 1990, p. 26–34 (Scientific American, August 1990, vol. 263, 1 2). (Rus.)
14. Selco D. J. Amyloid Protein and Alzheimer's Disease//V Mire Nauki, [1]1, 1992, p. 28–36 (Scientific American, November 1991, vol. 265, [1]5). (Rus.)

What is claimed is:

1. A substance for human and animal use, e.g., for therapeutic, prophylactic, alimentary or hygienic purposes comprising a complex of at least one medicament with at least one organogermanium compound (OGC), characterized in that the complex has the general formula (I):

$$L_k(OGC)_m(Solv.)_n \quad (I)$$

Where
$k \geq 1$
$m \geq 1$
$n \geq 0$
L: a medicament
Solv.: an inorganic or organic solvent
the OGC corresponding to the general formula (II):

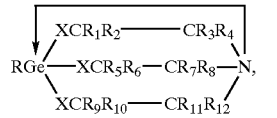

(II)

Where:
R: an organic radical comprising hydroxyl, thiohydroxyl, methyl, ethyl or adamantyl;
or an elementoorganic radical comprising silicium or germanium, such as —OSiCH$_3$ or —OGeCH$_3$;
R$_1$–R$_{12}$: hydrogen, or an organic radical, or oxygen as a substitution of anyone of the groups R$_1$R$_2$, R$_5$R$_6$ and R$_9$R$_{10}$
X: oxygen or sulfur.

2. A substance according to claim 1, wherein the OGC is selected from:
1-hydroxy-1-germa-2,8,9-trioxa-5-azatricyclo-(3.3.3.0$^{1,5}$)undecane; 1-thiohydroxy-1-germa-2,8,9-trioxa-5-azatricyclo(3.3.3.0$^{1,5}$)undecane; 1-methyl-1-germa-2,8,9-trioxa-5-azatricyclo(3.3.3.0$^{1,5}$)undecane-3-one; 1-ethyl-1-germa-2,8,9-trioxa-5-azatricyclo(3.3.3.0$^{1,5}$)undecane-3-one; 1-adamantyl-1-germa-2,8,9-trioxa-5-azatricyclo(3.3.3.0$^{1,5}$)undecane; 1-adamantyl-1-germa-2,8,9-trioxa-5-azatricyclo(3.3.3.0$^{1,5}$)undecane-3,7-dione; 1-methyl-1-germa-2,8,9-trioxa-5-azatricyclo-(3.3.3.0$^{1,5}$)undecane-3,7,10-trione; 1-hydroxy-1-germa-2,8,9-trioxa-3-methyl-5-azatricyclo-(3.3.3.0$^{1,5}$)undecane; 1-hydroxy-1-germa-2,8,9-trithio-5-azatricyclo(3.3.3.0$^{1,5}$)undecane.

3. A substance according to claim 1 wherein said at least one medicament or biologically active compound is selected from the following medicaments:
antiviral medicaments: Midantanun, Remantadinum, Zidovodine (Retrovir), Virolex Vidarabinum, Idoxuridine, Metisazonum, Oxolinum, Ganciclovir, Ribamidil; analgesic and antiinflamatory medicaments: acetyl-salicylic acid, methylsalicylate, salicylamide Mesalazine, Amidopyrinum, Analginun, Butadionum, Paracetamolum, Ibuprophenum, Naproxenum, Piroxicam, Sulindac, Dimexidum; antibacterial medicaments: Benzylpenicillinum-nalrium, Oxacillinum-natrium, Ampicilinum, Carbenicillinum disodium, Cefaloridinum, Cefalexinum, Cefaclorum, Erythromycinum, Oleandomycini phosphas, Tetracyclinum, Oxytetracyclinum dihydras, Doxycyclini dihydrochioridum, Metacyclin, Laevomycetinum, Streptomycine sulfate, Neomycinum, Kanamycinum, Gentamycini sulfas, Sisomicini sulfas, Amikacin sulfate, etc.; sulfamide medicaments: Sulfadimezinum, Aethazolum, Urosulfanum, Sulphapyridazinum, Sulfadimethoxinum, Phtalazolum, etc.; antituberculousis medicaments: Isoniacidum, Rifampicinum, Ethambutol, Ethionamide, Pirazinamide, Cycloserine, Florimicini sulfas; antitumor medicaments: Dopanum (Chlorethylaminouracil), Sarcolysinum (Racemelfalanum), Cyclophosphane Chlorbutinum, Thiophosphamidum, Nitrosomethylurea, Myelosanum (Busulfan), Methotrexatum, Mercaptopurinum Fluorouracil Fluorofur, Dactinomycinum, Olivomycinum, Rubomycini hydrochloridum, Colchaminum, Vinblastine, Vinicristine, Testosteroni propionas, Testoenatum, Synoestrolum, Phosphoestrolum, Aethyniloestradiolum, Hydrocortisonum, Prednisolone, Dexamethasonum, Triamcinolone, Cisplatin; antiepileptic medicaments: Phenobarbitalum, Diphieninum (Phenytoinum), Hexamidinum (Primidone), Sodium valproate, Lorazepam, Carbamazepin, Sibazonum (Diazepam), Trimethinum (Trimethadionum), Ethosuximidum; medicaments for Parkinson's syndrome: Levodopa, Cyclodolum, Mydocalm, Bromocryptinum, Carbidopa, Benserazide; tranquilizers: Chlozepidum, Diazepam, Mezapamum, Phenazepamum (Fenazepam); nootropic medicaments: Pyracetamum, Aminalonum; vitamins: A, B$_1$, B$_2$, D$_2$, D$_3$, E, K$_1$, K$_2$, PP, B$_5$, B$_6$, B$_{12}$, B$_c$, C, P; medicaments for treatment of schizophrenia: Aminazium, Propazinum, Aethaperazinum; medicaments for the treatment of cardiovascular system: Diazolum, NoSpa, Papaverini hydrochloridum, Nitroglycerol, Erynitum, Validolum, Digitoxin, Celanidum, Quinidine Sulfate, Lidocaini hydrochloridum, Amiodaronum, Ornidum, Mesatonum;
Aminoacids: glycine, alanine, valine, leucine, lysine, arginine, serine, cysteine, etc.

4. A substance according to claim 1 wherein said inorganic solvent is water.

5. A substance according to claim 1 wherein said organic solvent is selected from the following compounds: alcohols, polyols, ethers, esters, carboxylic acids, aminoalcohols, amides, sulphoxydes.

6. A medicament characterized in that it comprises a substance according to claim 1.

7. A food additive characterized in that it comprises a substance according to claim 1.

8. A hygienic product characterized in that it comprises a substance according to claim 1.

9. A cosmetic product characterized in that it comprises a substance according to claim 1.

10. A cream for external application to the human or animal body characterized in that it comprises a substance according to claim 1.

11. A lip stick characterized in that it comprises a substance according to claim 1.

12. A lotion characterized in that it comprises a substance according to claim 1.

13. A tooth paste characterized in that it comprises a substance according to claim 1.

14. A shampoo characterized in that it comprises a substance according to claim 1.

15. A soap characterized in that it comprises a substance according to claim 1.

16. A candle characterized in that it comprises a substance according to claim 1.

17. A theraputic method, in which the substance of claim 1 is applied perorally, as injections or externally in a dosage of 0.001 to 0.1 g of organogermanium compound per day.

18. A substance according to claim 1 wherein the medicament is selected from:

a medicament for treatment of viral diseases selected from: Virolex, Vidarabinum, Idoxuridine, Remandatinum, Midantanum, Dibasolum, Zidovudine;

a medicament for treatment of Nervous diseases selected from: Phenobarbitalum, Dipheninum, Hexamidinum, Midantanum, Levodopa, Aminazinum, Meterazinum, Chlorprotexenum, Diazepam, Phenazepanum, Mezapamum.

19. A substance for human and animal for therapeutic purpose comprising a complex of at least one medicament with at least one organogermanium compound (OGC), characterized in that the complex has the general formula (I):

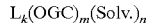

$$L_k(OGC)_m(Solv.)_n \qquad (I)$$

Where k≧1 m≧1 n≧0

L: a medicament

Solv.: an inorganic or organic solvent the OGC corresponding to the general formula (II):

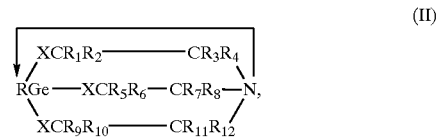

(II)

Where:

R: an organic radical comprising hydroxyl, thiohydroxyl, methyl, ethyl or adamantyl;

or an elementoorganic radical comprising silicium or germanium, such as —OSiCH$_3$ or —OGeCH$_3$;

$R_1$–$R_{12}$: hydrogen, or an organic radical, or oxygen as a substitution of anyone of the groups $R_1R_2$, $R_5R_6$ and $R_9R_{10}$ X: oxygen or sulfur;

wherein the medicament is selected from:

a medicament for treatment of viral diseases selected from: Virolex, Vidarabinum, Idoxuridine, Remandatinum, Midantanum, Dibasolum, Zidovudine;

a medicament for treatment of Nervous diseases selected from: Phenobarbitalum, Dipheninum, Hexamidinum, Midantanum, Levodopa, Aminazinum, Meterazinum, Chlorprotexenum, Diazepam, Phenazepanum, Mezapamum.

20. A substance according to claim 19, wherein the OGC is selected from:

1-hydroxy-1-germa-2,8,9-trioxa-5-azatricyclo-(3.3.3.0$^{1,5}$)undecane; 1-thiohydroxy-1-germa-2,8,9-trioxa-5-azatricyclo(3.3.3.0$^{1,5}$)undecane; 1-methyl-1-germa-2,8,9-trioxa-5-azatricyclo(3.3.3.0$^{1,5}$)undecane-3-one; 1-ethyl-1-germa-2,8,9-trioxa-5-azatricyclo(3.3.3.0$^{1,5}$)undecane-3-one; 1-adamantyl-1-germa-2,8,9-trioxa-5-azatricyclo(3.3.3.0$^{1,5}$)undecane; 1-adamantyl-1-germa-2,8,9-trioxa-5-azatricyclo(3.3.3.0$^{1,5}$)undecane-3,7-dione; 1-methyl-1-germa-2,8,9-trioxa-5-azatricyclo-(3.3.3.0$^{1,5}$)undecane-3,7,10-trione; 1-hydroxy-1-germa-2,8,9-trioxa-3-methyl-5-azatricyclo-((.3.3.0$^{1,5}$)undecane; 1-hydroxy-1-germa-2,8,9-trithio-5-azatricyclo(3.3.3.0$^{1,5}$)undecane.

21. A substance according to claim 19, wherein said inorganic solvent is water.

22. A substance according to claim 19, wherein said organic solvent is selected from the following compounds: alcohols, polyols, ethers, esters, carboxylic acids, aminoalcohols, amides, sulphoxydes.

23. A medicament characterized in that it comprises a substance according to claim 19.

24. A therapeutic method, in which the substance of claim 19 is applied perorally, as injections or externally in a dosage of 0.001 to 0.1 g of organogermanium compound per day.

* * * * *